United States Patent [19]

Lee et al.

[11] Patent Number: 5,211,924

[45] Date of Patent: * May 18, 1993

[54] METHOD AND APPARATUS FOR INCREASING CONVERSION EFFICIENCY AND REDUCING POWER COSTS FOR OXIDATION OF AN AROMATIC ALKYL TO AN AROMATIC CARBOXYLIC ACID

[75] Inventors: Myon K. Lee, Wheaton; William F. Huber, Jr., Naperville, both of Ill.

[73] Assignee: Amoco Corporation, Chicago, Ill.

[*] Notice: The portion of the term of this patent subsequent to Apr. 7, 2009 has been disclaimed.

[21] Appl. No.: 162,043

[22] Filed: Feb. 29, 1988

[51] Int. Cl.⁵ .................................. B01J 19/18
[52] U.S. Cl. ........................ 422/225; 366/279; 366/325; 366/327; 366/329; 366/330; 416/223 R; 416/231 A; 422/224; 422/226; 422/228; 422/234
[58] Field of Search ............... 422/224, 225, 226, 228, 422/234; 435/305, 306, 307, 315, 316; 210/208, 213, 219; 416/223 R, 231 A; 366/279, 325, 327, 329, 330

[56] References Cited

U.S. PATENT DOCUMENTS

| | | | |
|---|---|---|---|
| 62,320 | 2/1867 | Decker | 366/329 |
| 2,015,244 | 9/1935 | Stockdale | 422/225 |
| 2,245,588 | 6/1941 | Hughes | 366/329 |
| 2,348,124 | 5/1944 | Green | 210/208 |
| 2,391,738 | 12/1945 | Prager | 210/208 |
| 2,425,371 | 8/1947 | Green | 210/208 |
| 2,964,301 | 12/1960 | Bosse | 366/329 |
| 3,300,047 | 1/1967 | Hirsch | 210/208 |
| 4,438,074 | 3/1984 | Wilt | 422/228 |

Primary Examiner—Robert J. Warden
Assistant Examiner—Timothy M. McMahon
Attorney, Agent, or Firm—Gunar J. Blumberg; Wallace L. Oliver; Frank J. Sroka

[57] ABSTRACT

Improved mixing performance with reduced power input is obtained in an agitated oxidation reactor for converting an aromatic alkyl to the corresponding aromatic carboxylic acid by decreasing the clearance between the lowermost impeller element and the reactor bottom and by providing a flat blade turbine as the upper impeller element.

4 Claims, 2 Drawing Sheets

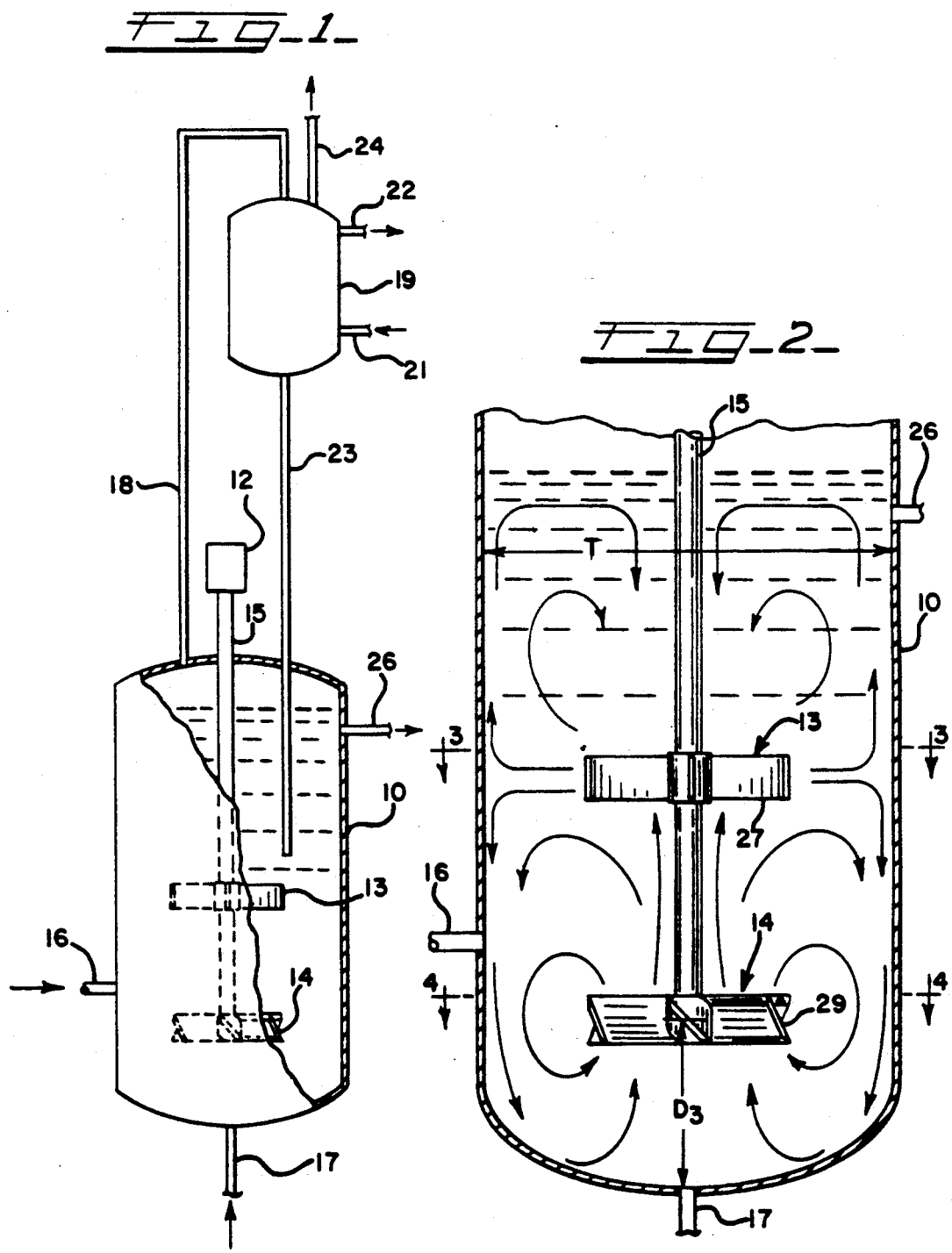

METHOD AND APPARATUS FOR INCREASING CONVERSION EFFICIENCY AND REDUCING POWER COSTS FOR OXIDATION OF AN AROMATIC ALKYL TO AN AROMATIC CARBOXYLIC ACID

FIELD OF THE INVENTION

This invention relates generally to the continuous, liquid-phase oxidation of an aromatic alkyl to an aromatic carboxylic acid, and principally to the liquid-phase oxidation of paraxylene to terephthalic acid. More particularly, the present invention concerns a method and apparatus for increasing reactor conversion efficiency and reducing power costs as well as for improving the quality of the produced aromatic carboxylic acid.

BACKGROUND OF THE INVENTION

Liquid-phase oxidation of an aromatic alkyl to an aromatic carboxylic acid is a highly exothermic chemical reaction. Volatilizable aqueous acidic solvents are used to contain the reaction mixture and to dissipate the heat of reaction. The oxidation of aromatic alkyls in the liquid phase to form aromatic carboxylic acids is generally performed in a vented, well-mixed oxidation reactor, with a substantial portion of the heat generated by the exothermic oxidation reaction being removed by refluxing a portion of the aqueous solvent and aromatic alkyl contained within the reactor as the reaction mixture.

The materials vaporized as a result of the heat generated in the exothermic reaction, together with unreacted oxygen and other aqueous components that may be present, pass upwardly through the reactor and are withdrawn from the reactor at a point above the reaction mixture liquid level in the reactor. The vapors are passed upwardly and out of the reactor to an overhead reflux condenser system where the vaporized solvent, water and aromatic alkyl are condensed. The condensed materials, now at a temperature less than the reactor contents' temperature, are returned to the reactor by gravity. The noncondensible gases, carried along with the vaporized reactor material, are vented.

In operation, the reactor is fed by a liquid feed stream containing the aromatic alkyl, aqueous acidic solvent and an oxidation catalyst. An oxygen-containing gas is separately introduced into the reactor for oxidizing the aromatic alkyl to aromatic carboxylic acid in the presence of the catalyst.

The reaction mixture contained in the reactor includes small crystals suspension of the produced aromatic carboxylic acid. Since the reaction mixture contains solid-phase and liquid-phase components, as well as the continuously introduced oxygen-containing gas, vigorous stirring of the reactor contents is necessary to suspend solids and to obtain a high quality product. The vigorous stirring is costly in terms of power input and maintenance; and even with high agitator power input the mixing effectiveness of prior systems has not been as good as desired.

In one system for the production of an aromatic carboxylic acid, the reaction takes place in a vertically disposed elongated vessel having a substantially cylindrical side wall and having an agitator mounted for rotation within the vessel on a shaft situated at about the axis of the vessel. The agitator drives an upper mixing element, or impeller, in the form of a 4-blade disc turbine at an intermediate location on the shaft and a lowermost mixing element, or impeller, in the form of a 4-blade turbine with pitched blades at the lower end of the shaft.

The disc turbine has a disc diameter of 0.6 times the turbine diameter; and each of its 4 blades has a radial length equal to 0.25 times the turbine diameter.

The bottom pitched blade turbine has a clearance clearance reactor bottom of about 0.35 to 0.39 times the inside diameter of the reactor vessel.

The blade thickness in the pitched blade turbine is about 0.0052 times the diameter of the lower mixing element. The cross section of each blade is rectangular.

A portion of the aromatic carboxylic acid produced in the course of the oxidation reaction forms finely divided solid crystals, because the product is nearly insoluble at the conditions of the reaction mixture. Because these crystals are of relatively higher density than the liquid in the reactor, a portion thereof tends to settle to the bottom of the reactor when the stirring is inadequate. Such settling can result in a buildup of solids in the reactor bottom which results in reactor burns or reactor fouling. In addition, in the stirred reactors prior to this invention, the stirring creates separate circulation loops, or cells, within the lower and upper portions of the reactor with little mixing between them, producing zones of poor mixing or dead spots.

The present invention, on the other hand, provides improved mixing effectiveness in the reactor vessel whereby zones of poor mixing are eliminated and solid crystals are suspended uniformly. Solid particles tending to settle at the bottom of the reactor vessel are impelled at relatively lower impeller speeds and relatively lower energy costs. An aromatic carboxylic acid of higher purity may be obtained as a result.

SUMMARY OF THE INVENTION

The present invention is an improvement in an apparatus and method for the continuous production of an aromatic carboxylic acid by liquid-phase oxidation of an aromatic alkyl in an oxidation reactor equipped with an axially mounted agitator provided with one impeller positioned at about midpoint of the reactor and another impeller on the same shaft near the reactor bottom. The improvement includes the substitution of a flat blade turbine with blades emanating substantially from the agitator shaft in lieu of the disc turbine heretofore used as an upper impeller element, and a decrease in the clearance between the lowermost impeller element and the reactor bottom from a conventional spacing of 0.35-0.39 times to a spacing of about 0.25 to about 0.33 times the inside diameter of the reactor vessel. Also contemplated are a decrease in the thickness of the blades of the lowermost impeller element from a conventional thickness of about 0.005 times to a thickness of about 0.002-0.004 times the diameter of the lower impeller, and impeller blades having profiled edges wherein the leading edge of the blade (in the direction of rotation) is longer than the trailing edge by an amount sufficient to provide an acute angle of 10°-50° at the leading edge. The foregoing agitator results in improved overall mixing at a relatively lower power input. Product quality is enhanced as well.

BRIEF DESCRIPTION OF THE DRAWINGS

FIG. 1 is a schematic diagram, partly in cross-section, showing the general configuration of the reactor of this invention;

FIG. 2 is a partial schematic cross-sectional view of the reactor (enlarged relative to FIG. 1 and with upper end broken away), showing the spatial relationship of the agitator elements and the flow paths obtained during mixing;

Figure 3:
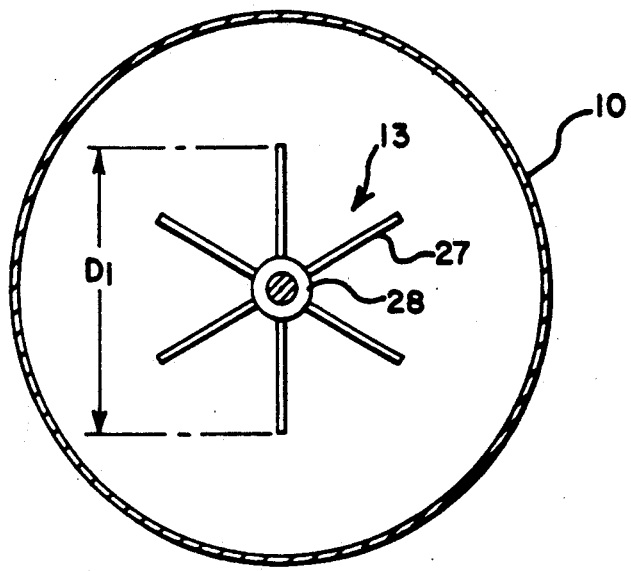
FIG. 3 is a cross-sectional view through plane 3—3 of FIG. 2.

The drawings of FIGS. 1 and 2 are schematic in nature and are intended to illustrate the novel features of this invention. Accordingly, details which are not necessary for an understanding of the present invention have been omitted.

DETAILED DESCRIPTION OF PREFERRED EMBODIMENTS

Aromatic carboxylic acid is produced in an oxidation reactor at an elevated temperature and pressure by liquid-phase, exothermic oxidation of an aromatic alkyl by an oxygen-containing gas in a vaporizable, aqueous acidic solvent medium. Oxidation of the aromatic alkyl to the aromatic carboxylic acid takes place in the aqueous acidic solvent medium in the presence of an oxidation catalyst. The conversion of aromatic alkyl to aromatic carboxylic acid is exothermic. Heat generated by the oxidation reaction is at least partially dissipated by vaporization of a portion of the solvent, water, aromatic alkyl and other vaporizable constituents of the reaction mixture present in the oxidation reactor. Vaporized reaction mixture constituents are withdrawn from the oxidation reactor, condensed in an overhead condenser system, and fed back into the oxidation reactor while uncondensed gases are discharged from the system.

A liquid feed stream for the oxidation reactor contains the aromatic alkyl, the acidic solvent medium, and an effective amount of an oxidation catalyst for effecting in the reactor a liquid-phase oxidation of the aromatic alkyl, in the presence of oxygen, to the aromatic carboxylic acid.

Referring to FIG. 1, an elongated, vertically-disposed, continuous stirred-tank oxidation reactor 10 for oxidizing an aromatic alkyl to an aromatic carboxylic acid is shown. The oxidation reaction is continuous and proceeds in the liquid phase. The reactor 10 includes an agitator 12 which drives upper mixing element, or upper impeller, 13 and lowermost mixing element, or lower impeller, 14, both fixed to an agitator shaft 15. The reactor 10 may further include internal baffles (not shown). Each mixing element is rotated by the shaft 15 in a generally horizontal plane at a preselected rotational speed so that the contents of the reactor 10 are well-mixed, as is discussed in detail below.

The contents of the reactor 10 are subjected to an elevated pressure and temperature sufficient to maintain the contained volatilizable solvent and aromatic alkyl substantially in the liquid state. A reflux loop, shown in FIG. 1, assists in controlling the oxidation reactor temperature.

An aromatic alkyl, such as paraxylene, and a volatilizable aqueous acidic solvent medium, such as a catalyst-containing aqueous acetic acid solution, are combined to form a mixture, which enters reactor 10 through conduit 16. An oxygen-containing gas is introduced into the bottom of the reactor 10 via a gas inlet line 17. The oxygen-containing gas serves to oxidize the aromatic alkyl to an aromatic carboxylic acid in the presence of the catalyst.

Heat of reaction in the reactor 10 vaporizes the volatilizable solvent, water and reaction mixture contained therein. A substantial portion of the heat generated by the exothermic reaction in the reactor 10 is removed from the reaction mixture by vaporization of the aqueous solvent and, to a lesser extent, the aromatic alkyl. The vaporized material and any unreacted oxygen and other components of the oxygen-containing gas fed to the reactor 10 pass upwardly through the reactor 10 and are withdrawn from the reactor 10 via the exit pipe 18. The vaporized materials and gases, contained within pipe 18, are received into an overhead condenser system such as the condenser 19, through which a cooling liquid is circulated, entering through inlet 21 and discharging through outlet 22. A condensed portion of the vapors passing into condenser 19 is returned to the reactor through conduit 23. An uncondensed portion is vented from the system through conduit 24.

In the reactor 10, the aromatic alkyl is oxidized by oxygen, usually introduced as air, in the presence of the catalyst, to form the desired aromatic carboxylic acid and intermediates thereto. A product stream is withdrawn as an effluent stream from the reactor 10 via the discharge pipe 26. The product stream is thereafter treated using conventional techniques to separate its components and to recover the aromatic carboxylic acid contained therein, usually by further crystallization liquid-solid separation and drying.

The distinctive features of the present invention are illustrated in greater detail in FIGS. 2 to 5. In FIG. 1 and the remaining FIGURES, like reference numerals have been assigned to like parts or elements. Further, for the sake of brevity, only those parts or elements of FIGS. 2 to 5 which have not been discussed in detail heretofore will be discussed at length hereinbelow.

Referring to FIGS. 2 and 3, upper impeller element 13 comprises a six-blade flat blade turbine, in which each blade 27 is flat and in a plane which is radial to shaft 15. The blades are substantially evenly spaced from each other and each blade extends substantially radially outwardly from a central inner shaft. This is in contrast to the disc turbines heretofore used in which the individual blades are relatively short and are connected to the inner shaft through a disc having a diameter about ⅔ that of the turbine. Each blade in FIG. 3 is attached to shaft 15 through hub 28 which is of relatively small diameter and provides a substantially unobstructed flow path through the blades.

The turbine diameter (D1 in FIG. 3) is about 0.45 to about 0.55 times the inner diameter of the vessel.

Figure 4:
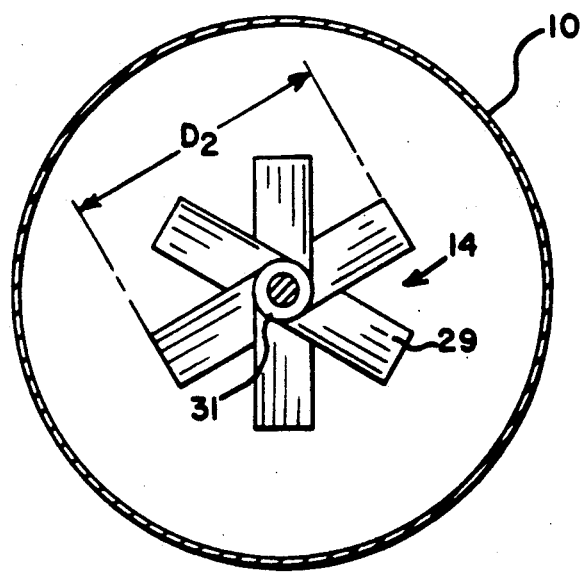
FIG. 4 is a cross-sectional view through plane 4—4 of FIG. 2.
Figure 5:
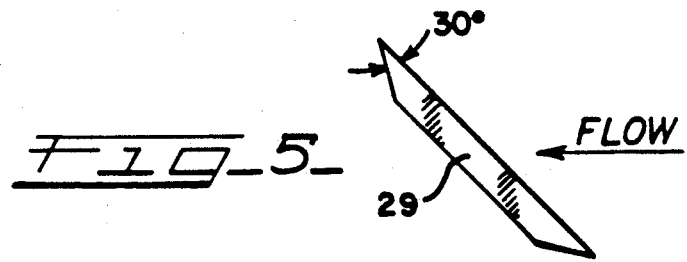
FIG. 5 is a cross-sectional view of one of the blades in the pitched blade turbine shown in FIG. 4.

As shown in FIGS. 2 and 4, lowermost impeller element 14 comprises a six-blade pitched blade turbine, in which each blade 29 is pitched at an angle in the range of about 30° to about 60°. A preferred blade pitch angle is in a range of about 40° to about 50°. A particularly preferred blade pitch is an angle of about 45°. The blades are spaced substantially evenly from each other. Each blade is attached to shaft 15 through hub 31 of relatively small diameter.

Each of the pitched blades 29 has a thickness, preferably of about 0.002 to about 0.004 times the diameter of the lower impeller. Both edges of each blade are preferably sharpened, as shown in cross-section of FIG. 5, by removing the lower corner of both edges of the blade, to produce an angle between the edge and the surface of the blade in the range of about 10° to about 50°. In comparative tests utilizing a 4-blade pitched blade turbine, the thinning and profiling of the turbine blades in accordance with one aspect of the invention decreased power requirements for the turbine by about 7%.

The diameter of the pitched blade turbine, shown in FIG. 4 as D2, is about 0.50 to 0.55 times the inner diameter of the vessel.

The spacing along the center line of the reactor between the mid-level of the blades of the pitched blade turbine and the bottom wall of the reactor is also a feature of this invention. This particular dimension is shown in FIG. 2 as dimension D3 and is about 0.25 to about 0.33 times the inner diameter of the reactor vessel.

The flow patterns within the body of liquid which are generated by the action of the mixing elements, or impellers, are shown in FIG. 2. It should be understood, however, that FIG. 2, being planar, cannot depict the rotational element of the flow around the inner wall of the vessel and around shaft 15.

At mixing element 13, the rotating flat blades impel the surrounding fluid radially outwardly toward the cylindrical wall of vessel 10. Upon approach to the cylindrical wall, a portion of the fluid is diverted downwardly and a portion is diverted upwardly. The upwardly-directed stream continues to flow, primarily along the wall, to the top of the liquid body and then flows inwardly toward the shaft and finally downwardly toward the center of the upper impeller.

The downwardly-directed stream at the vessel wall continues its downward path, primarily along the wall until it is diverted toward the center of the vessel by its curved bottom. It is urged upwardly by the action of the lowermost impeller, as described below. As this stream moves upwardly and rotationally along the bottom wall of the reactor it sweeps up any solid particles that tend to be deposited at the reactor bottom. This fluidizing action is enhanced by the relatively shorter spacing at D3 than heretofore employed between the reactor bottom and the lower impeller 14.

The rotating pitched blades of lowermost mixing element 14 impart a swirling motion to the slurry contents of the vessel outwardly and upwardly. The portion of the fluid impelled rotationally and outwardly merges with the downwardly flowing stream from the upper impeller near the cylindrical vessel wall.

The upward impelling by the rotation of lowermost mixing element 14 pulls liquid from the bottom wall of the vessel and directs it upwardly around shaft 15. In the mixing systems prior to this invention which utilized disc turbines, the upwardly flowing stream around the shaft was diverted outwardly toward the vessel wall by the impervious disc carrying the turbine blades. There were thus created two discrete mixing cells, or circulation loops, within the body of liquid with only a limited interchange being possible between them at the location where the outwardly flowing stream from the disc turbine impinged on the vessel wall and split into upwardly and downwardly flowing portions.

In addition, the fluid motions in the regions just above and below the center of the disc are like stagnant flows and thus fluid mixing in these regions is poor relative to other regions of the fluid body. Flow visualization experiments confirmed this, revealing that the region of the least efficient mixing (dead spots) in the vessel was the immediate neighborhood of the center of the disc. Impurities detrimental to the product quality are produced in the region of poor mixing (dead spots) where the dissolved oxygen concentration is low.

In contrast, the structure of the flat blade turbine serving as the intermediate mixing element in accordance with the present invention permits an upwardly flow therethrough because each blade extends substantially to the shaft and thus provides a flow path and substantially greater intermixing between upper and lower portions of the body of liquid at a relatively lower power consumption. This results in greater product uniformity and higher product purity as well.

The invention has been described with respect to its preferred embodiments. It will be understood by those skilled in the art that variations and modifications may be employed within the scope of the invention as defined in the claims hereinbelow.

I claim:

1. In a reactor suitable for the oxidation of an aromatic alkyl comprising a vertically disposed elongated vessel having a bottom and a substantially cylindrical side wall, said reactor having reactant inlet means and solids-containing reaction product outlet means, oxidizing gas inlet means at at least one location within the vessel and vent means, and an agitator adapted for rotation within the vessel on a shaft at about the axis of the vessel, the agitator having an upper mixing element and a lowermost mixing element, the improvement wherein the upper mixing element is an outwardly impelling element comprising a flat blade turbine provided with a plurality of blades substantially evenly spaced from each other and each in a plane radial to the shaft with each blade extending substantially to the agitator shaft, the flat blade turbine having a diameter about 0.45 to 0.55 times the inside diameter of the vessel, and wherein the lowermost mixing element is an outwardly impelling element comprising a pitched blade turbine having a diameter of about 0.5 to about 0.55 times the inside diameter of the vessel and provided with a plurality of pitched blades substantially evenly spaced from each other, each of the pitched blades having a leading edge and a trailing edge and a pitch in a range of about 30° to about 60°, the lowermost element being located so that a distance from its mid-level to the bottom of the vessel is about 0.25 to about 0.33 times the inside diameter of the vessel and the upper and lowermost mixing elements being spaced from one another at a distance sufficient to provide substantially uniform mixing of the entire content of said vessel upon rotation of the upper and lowermost mixing elements.

2. The apparatus of claim 1 wherein each of said upper mixing element and said lowermost mixing element has six blades.

3. The apparatus of claim 2 wherein each blade of said lowermost mixing element has a thickness of about 0.002 to about 0.004 times the diameter of said lowermost mixing element.

4. The apparatus of claim 3 wherein both edges of each blade of said lowermost mixing element are sharpened so that each edge produces an included angle between said edge and the surface of said blade in the range of about 10° to about 50°.

* * * * *